United States Patent [19]

Bottiger et al.

[11] Patent Number: 5,918,254

[45] Date of Patent: Jun. 29, 1999

[54] LOW CONCENTRATION AEROSOL GENERATOR

[75] Inventors: Jerold R. Bottiger, Aberdeen; Paul J. DeLuca, Joppatowne, both of Md.

[73] Assignee: The United States of America as represented by the Secretary of the Army, Washington, D.C.

[21] Appl. No.: 08/837,362

[22] Filed: Apr. 17, 1997

[51] Int. Cl.[6] .................................................. G01N 1/00
[52] U.S. Cl. ............................................................ 73/1.06
[58] Field of Search ................................. 73/1.01–1.03, 73/1.05, 1.06, 28.01, 865.5, 863.12; 250/252.1; 324/71.4; 356/36, 243

[56] References Cited

U.S. PATENT DOCUMENTS

| | | | |
|---|---|---|---|
| 4,917,830 | 4/1990 | Ortiz et al. | |
| 5,259,254 | 11/1993 | Zhu et al. | 73/863.12 |
| 5,298,967 | 3/1994 | Wells | 73/61.72 |

*Primary Examiner*—Robert Raevis
*Attorney, Agent, or Firm*—Edward L. Stolarun; Ulysses John Biffoni

[57] ABSTRACT

A low concentration aerosol generator capable of generating aerosol particles of a known particle size and count is disclosed. The device includes a substantially hollow drying chamber having a first end, a second end, and a gas circulation means for circulating a gas in a flow through the drying chamber via an inlet means and an outlet means. The first end of the drying chamber has an aerosol droplet generator capable of generating aerosol droplets of a predetermined size and which droplets contain a detectable sample within the drying chamber. The second end of the drying chamber includes a delivery tube having a first orifice arranged within the drying chamber for receiving the detectable sample and a second orifice for allowing the detectable sample to exit the drying chamber. The gas circulation means includes means for generating and regulating the flow of the gas through the drying chamber. The invention also includes a method of generating and delivering a sample particle in a low velocity air stream to an analyzing instrument using the aforementioned device.

17 Claims, 4 Drawing Sheets

LOW CONCENTRATION AEROSOL GENERATOR

GOVERNMENT INTEREST

The invention described herein may be manufactured, licensed, and used by or for the U.S. Government.

BACKGROUND OF THE INVENTION

1. Field of the Invention

The present invention relates to an apparatus useful in generating and counting aerosol particles. In particular, the invention relates to an apparatus which is capable of generating and counting low concentrations of individual aerosol particles.

2. Description of the Prior Art

Recently, governments have become increasingly interested in identifying and controlling developed biological warfare agents. These agents are highly dangerous and extreme caution must be used in the handling of these agents. In the event that these agents are deployed, part of the initial defense includes the rapid and accurate detection of the agents.

Instruments which are used to detect biological warfare agents include apparatus which analyze aerosols such as the CB mass spectrometer or a UV fluorescence-based detector. The instruments must be properly calibrated before being employed. Calibration of these instruments requires the use of aerosol particles that are agglomerates of individual bacteria cells or spores. In the past, the aerosolized particles, nebulizers, sprayers fluidized beds, sonic nozzles, etc. have been used. These apparatus, however, produce copious amounts of aerosols which may have a more or less compact size distribution depending upon the specific technique used to generate the aerosol. Measuring the amount of individual aerosol particles generated is often difficult and usually only approximated. In fact, the aerosols are measured by the mass of the material consumed by the apparatus rather than the actual amount of aerosol particles generated. In addition, although there are currently available scientific droplet generators capable of forming droplets of a uniform size such as the Vibrating Orifice Aerosol Generator (TSI Inc, Minneapolis, Minn.), they are not, however, suitable for the calibration needs described above. Such devices are of a high speed free-running nature and do not allow exact counts of small numbers of aerosol particles made.

In view of the need to more accurately calibrate biological warfare detection apparatus, there is a need for improved aerosol generating apparatus. In particular, there is a need for an apparatus which allows an investigator to control the amount, size and rate of generation of aerosol particles. There is also a need in this field to provide a means of delivering aerosol particles in a low velocity air-stream which is suitable for direct injection into analyzing instruments. Then present invention addresses these needs.

SUMMARY OF THE INVENTION

In view of the foregoing, it is therefore an object of the present invention to provide an improved aerosol particle generation apparatus useful in the calibration and profiling of aerosol analyzing instruments which are used to detect biological warfare agents.

It is a further object of the invention to provide an aerosol generating apparatus which is capable of generating aerosol particles of a known particle size, having a known particle count, and in low concentrations.

In one aspect of the invention, these and other objects of the invention are achieved by a sample conditioning device for conditioning an aerosol droplet containing a detectable sample. The device or apparatus comprises:

a substantially hollow drying chamber having a first end, a second end, and a gas circulation means for circulating a gas in a flow through said drying chamber via an inlet means and an outlet means;

said first end of said drying chamber having an aerosol droplet generator capable of generating aerosol droplets of a predetermined size containing a detectable sample within said drying chamber;

said second end of said drying chamber including a delivery tube having a first orifice arranged within said drying chamber for receiving said detectable sample and a second orifice for allowing said detectable sample to exit said drying chamber; and said gas circulation means having means for generating and regulating said flow of said gas through said drying chamber.

In a second embodiment there is provided a method of delivering a sample particle in a low velocity air stream to an analyzing instrument such as CB mass spectrometer. The method includes:

a) generating a liquid droplet containing sample particles such as via a sample conditioning device as described above;

b) drying the liquid droplets so that only the dried sample particles remain; and c) directing the sample particles to analyzing instruments, preferably at a low velocity.

The advantages of the present invention include the fact that it provides an unique degree of control over the aerosol, allowing the investigator to choose the material of which the particles are to be made, the size of the particles, the rate of generation, the total number of individual particles generated, and it delivers the particles in a low velocity air stream suitable for direct injection into analyzing instruments.

An additional benefit, particularly when aerosols of hazardous materials are required, is that very small quantities of aerosol are generated and the aerosol is confined to the generator and the analyzer; it is not necessary to fill large chambers with lethal materials. In certain preferred embodiments, the parts of the apparatus that hold the sample material, i.e. the droplet generator and/or drying chamber are disposable.

DETAILED DESCRIPTION OF THE PREFERRED EMBODIMENT

In one aspect of the present invention, the present invention includes an apparatus capable of generating and optionally counting low concentrations of individual aerosol sample particles.

The sample particles generated by the apparatus of the present invention have the properties that they are dry and of nearly uniform size; the size can be chosen from the range from about 2 to 10 microns. The generated sample particles result from the evaporation of uniformly sized water droplets containing the material of interest, either in solution or suspension. The final particles can accordingly be either single crystals or aggregates of smaller particles. The rate of generation may be varied from zero up to several thousand particles per second. The apparatus keeps an exact count of the number of particles generated, and may be configured to automatically stop after generating a predetermined number of sample particles.

The invention includes a sample conditioning device for conditioning an aerosol droplet containing a detectable sample. The apparatus comprises:

a substantially hollow drying chamber having a first end, a second end, and a gas circulation means for circulating a gas in a flow through the drying chamber via an inlet means and an outlet means;

the first end of the drying chamber having an aerosol droplet generator capable of generating aerosol droplets of a predetermined size containing a detectable sample within the drying chamber;

the second end of the drying chamber including a delivery tube having a first orifice arranged within the drying chamber for receiving the detectable sample and a second orifice for allowing the detectable sample to exit the drying chamber; and the gas circulation means having means for generating and regulating the flow of the gas through the drying chamber.

In this aspect of the invention, the apparatus 1 comprises three sections: 1) a liquid droplet generator, 2) a drying chamber with air control, and 3) controlling electronics.

1. Liquid Droplet Generator

Figure 1:
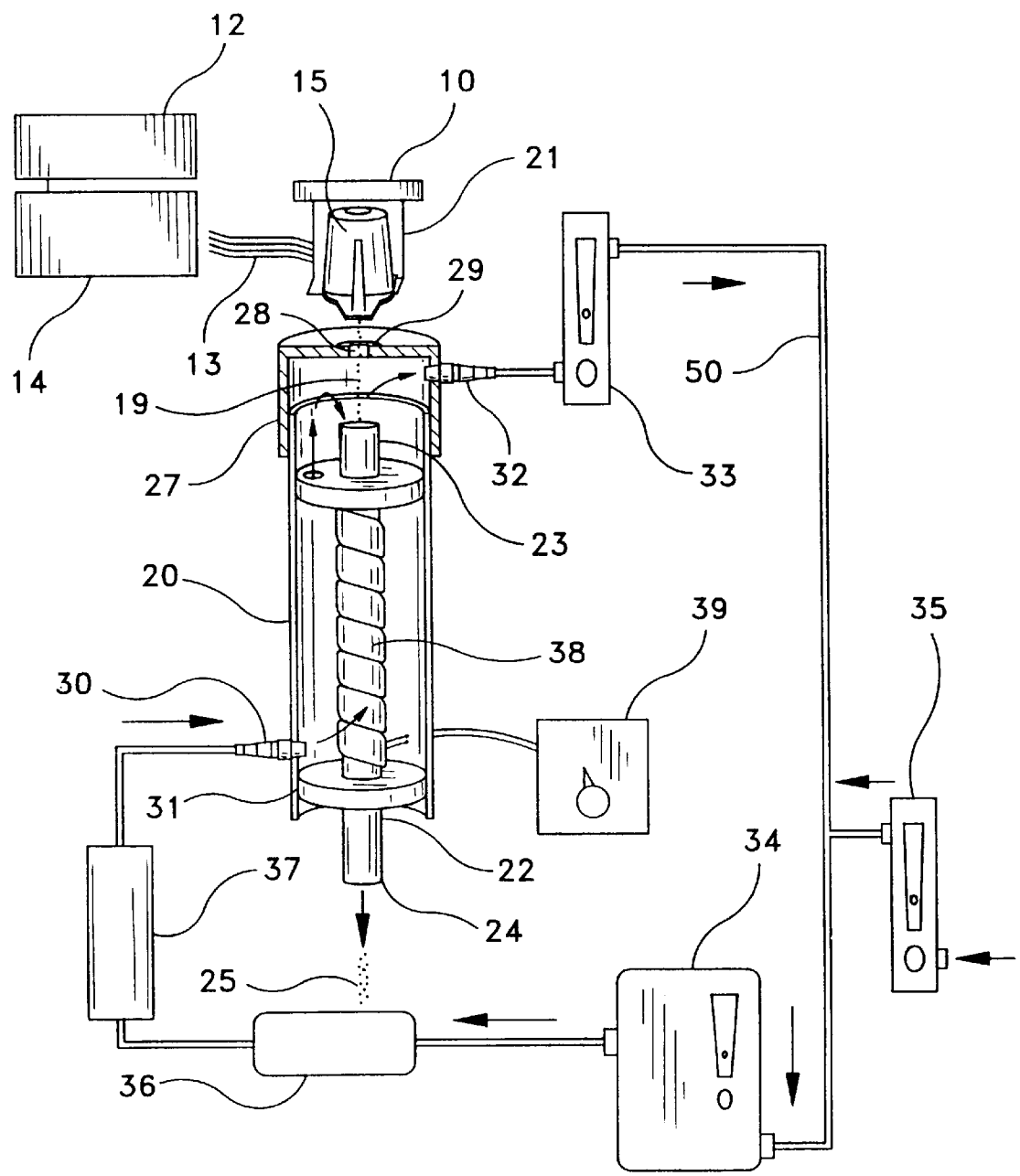
FIG. 1 is a side view of an apparatus in accordance with the present invention.
Figure 2:
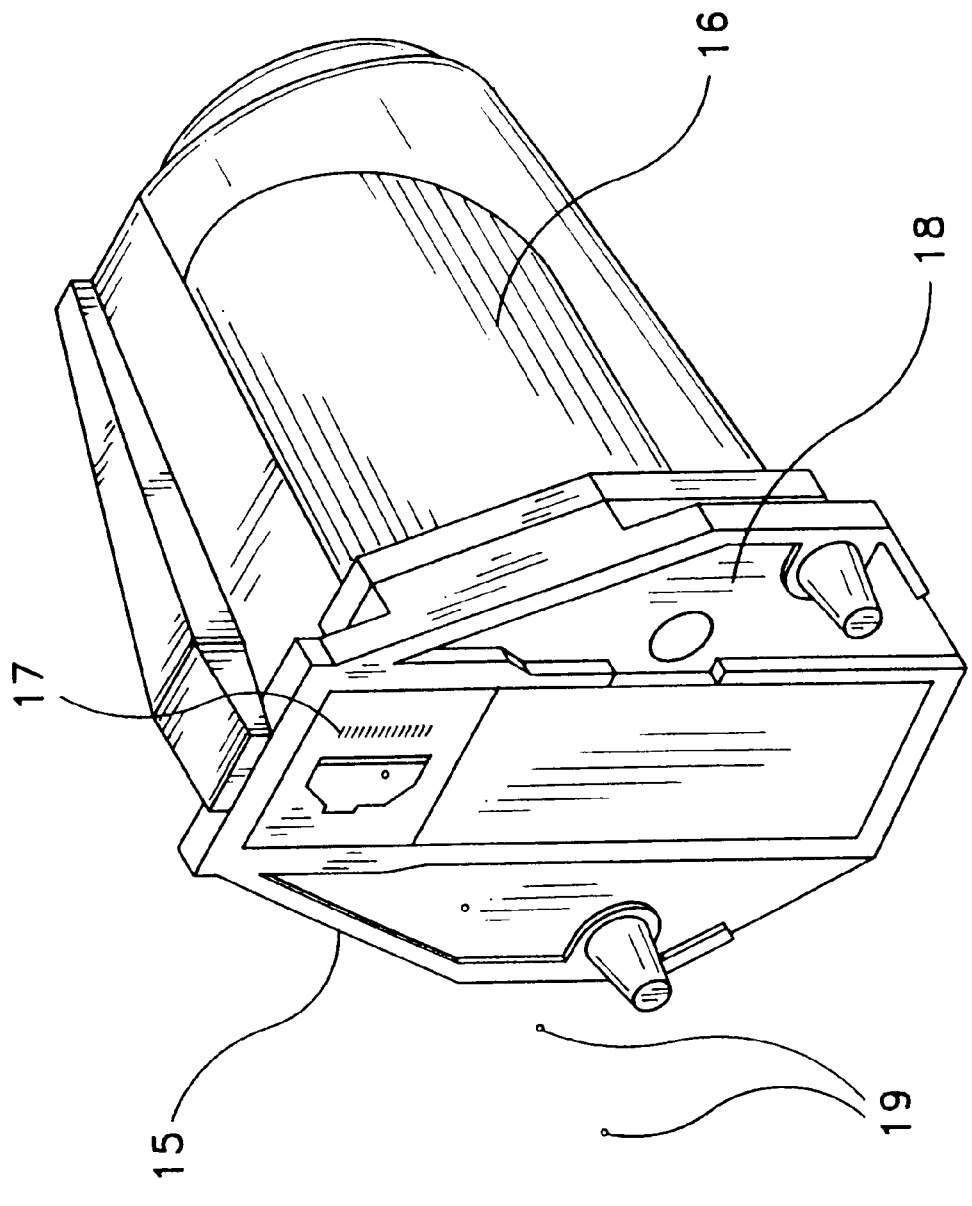
FIG. 2 is a perspective view of a droplet generator used in conjunction with a preferred embodiment of the present invention.

Referring now to FIGS. 1 and 2, a preferred aspect of the invention is described. The apparatus 1 includes a droplet generator 10 which is capable of emitting one liquid droplet, of a substantially fixed size. Preferably, the droplets are generated each time a single electrical pulse (of appropriate amplitude and duration) from the pulse generator 12 via a suitable pulse controller 14 and conductor ribbon 13 is applied to the droplet generator 10.

For purposes of illustration and not limitation, the liquid droplet generator 10 includes a disposable ink-jet cartridge 15 such as those used in the Hewlett-Packard line of ThinkJet and QuietJet printers, sold as HP part number 92261A. The cartridge incorporates a pliable bladder 16 that holds approximately 4 ml of ink. Access holes can be drilled through the face 18 and the ink in the reservoir removed and replaced with a solution or slurry of water and the material of interest. Alternatively, and more simply, unfilled cartridges may be purchased from HP and loaded and sealed by the user.

The solution droplets 19 are ejected from a plurality of nozzles 17 found as microscopic holes in the faceplate 18 on a line, which for example in the HP inkjet cartridge 15, is about 4 mm long. The nozzles 17 are served by separate electrical conductors and liquid feed channels (not shown), and can be fired independently of each other. A nozzle is fired by applying sufficient voltage, i.e about 24 volts to its circuit for about 6 microseconds. The current heats a tiny resistance heater that causes a bubble to form and expand in the feed channel, forcing a droplet 19 of solution, about 60 microns in diameter, out through the nozzle 17. In one preferred aspect, the device fires the nozzles one at a time in sequential order at a rate set by the user.

In FIG. 1, the modified ink-jet cartridge acting as a droplet generator 10 is to be physically attached to the drying chamber 20 and electrically interfaced to a pulse controller 14 using a printer carriage assembly 21 (available from Hewlett-Packard as a replacement part, part number 02225-60914). The assembly includes a snap-in holder for the cartridge and a conductor ribbon 13 for electrical connections.

It is to be understood that other droplet generators may be used in place of a ThinkJet cartridge. For example, newer designs of ink cartridges, both bubble and piezoelectric types can be modified in the manner described herein in order to be included in the apparatus 1. Another appropriate droplet generator is the microparticle generator made by Uniphoton Systems Inc, Brooklyn, N.Y.

2. Drying Chamber

In FIG. 1, the drying chamber 20 is shown as a closed plastic chamber having a central metal delivery tube 22 having a first orifice 23 and a second orifice 24 that allow dried sample particles 25 to pass through the drying chamber. The delivery tube 22 extends through the second end of the drying chamber 20 and into the interior of the drying chamber a distance which is sufficient to allow the delivery tube 22 to receive the droplets 19 generated by the droplet generator. The carriage assembly 21 holding the droplet generator, i.e. ink-jet cartridge, 10 is mounted onto the first end of the drying chamber 20. Referring now to FIGS. 1 and 2, the droplet generator cartridge is shown snap-mounted into the carriage assembly 21; its nozzles 17 pointing downward through a hole 28 in the center of the first end of the drying chamber 27. A rubber gasket 29 forms a seal between the drying chamber first end cap 27 and the cartridge face plate 18 surrounding the nozzles 17.

In a preferred embodiment, a constant stream of gas, preferably dry air, is pumped into the drying chamber 20 through an inlet means 30 found in the second end of the drying chamber 20. The first end of the drying chamber 20 also includes and outlet means 32 for allowing the constant stream to circulate through the drying chamber. In operation, the air flow divides between two exit ports, i.e the outlet 32 and the first orifice of the delivery tube 23 to leave the drying chamber. Part of the air flows down the delivery tube to carry out drying and dried particles 25 and the remainder—the winnowing flow—flows across the drying chamber and leaves through the outlet 32 shown near the top of the drying chamber. A flowmeter with a metering valve 33 measures and allows adjustment of the winnowing flow. The dried particle exits the delivery tube at a low velocity (approximately 0.5 liters/min.) air stream which is suitable for direct injection into analyzing instruments which need to be calibrated in their use as detectors for biological warfare agents. Examples of these analyzers are the CB mass spectrometer and UV fluorescence based detectors. Each of these devices require aerosol particles that are agglomerates of individual bacteria cells or spores in order to detect the presence of the biological warfare agents.

A diaphragm air pump 34 with an integral flowmeter powers the circulation, and allows one to set and measure the flow into the drying chamber. The air pulled into the diaphragm pump consists of the winnowing flow plus ambient air drawn through a flowmeter 35 at a rate equal to the delivery tube flow. A tube of desiccant 36 dries the air leaving the diaphragm pump. A filter 37 after the tube of desiccant insures that air entering the drying chamber is particle free. The flow from the outlet 32 back to the inlet 30 is accomplished by tubing 50.

The distance from the droplet generator, depicted in FIG. 1 as a modified ink jet cartridge, to the first orifice (entrance) 23 of the delivery tube 22 is important for proper operation of the device. For example, a particle projected into still air travels a distance known as the stop distance before losing its initial momentum. The stop distance for the principal droplets (e.g. ~60 microns in diameter) ejected from the modified ThinkJet cartridge was measured to be about 2 inches. Thus, in one preferred embodiment the gap between the nozzles 17 and the delivery tube first orifice 23 is about two inches. It will be understood that the distance between these points can vary according to the needs of the artisan and will depend, to a certain extent upon the design of the drying chamber, particle samples desired, etc. The full size particle emitted from a nozzle with each electrical pulse thus reaches and enters the delivery tube. It will quickly thereafter decelerate to its terminal falling velocity and slowly travel down the tube, slowing further as its water evaporates and finally emerging out the bottom as a particle of residue material embedded in the delivery tube air flow. One or two small liquid fragments frequently accompany the ejection of the main inkjet particle. Being less massive, their stop distance is much shorter and they will come to rest in the air before reaching the delivery tube entrance. Caught in the winnowing flow, they are swept from the drying chamber; only the main particles, one per pulse, are transported down the delivery tube.

One illustrative delivery tube is 0.5 inches in diameter and 11 inches long and has a delivery tube flow of about nominally 0.5 liters/minute. Therefore particles spend about four seconds in the tube. If this time is insufficient for drying the droplets at ambient temperature, the temperature of the drying chamber can be elevated up to about 200 degrees Fahrenheit using a heat source. In FIG. 1, the delivery tube 22 is shown wrapped with flexible electric heating tape 38. An electrical power controller 39, into which the heating tape is plugged, permits regulation of the temperature.

3. Controlling Electronics

Figure 3:
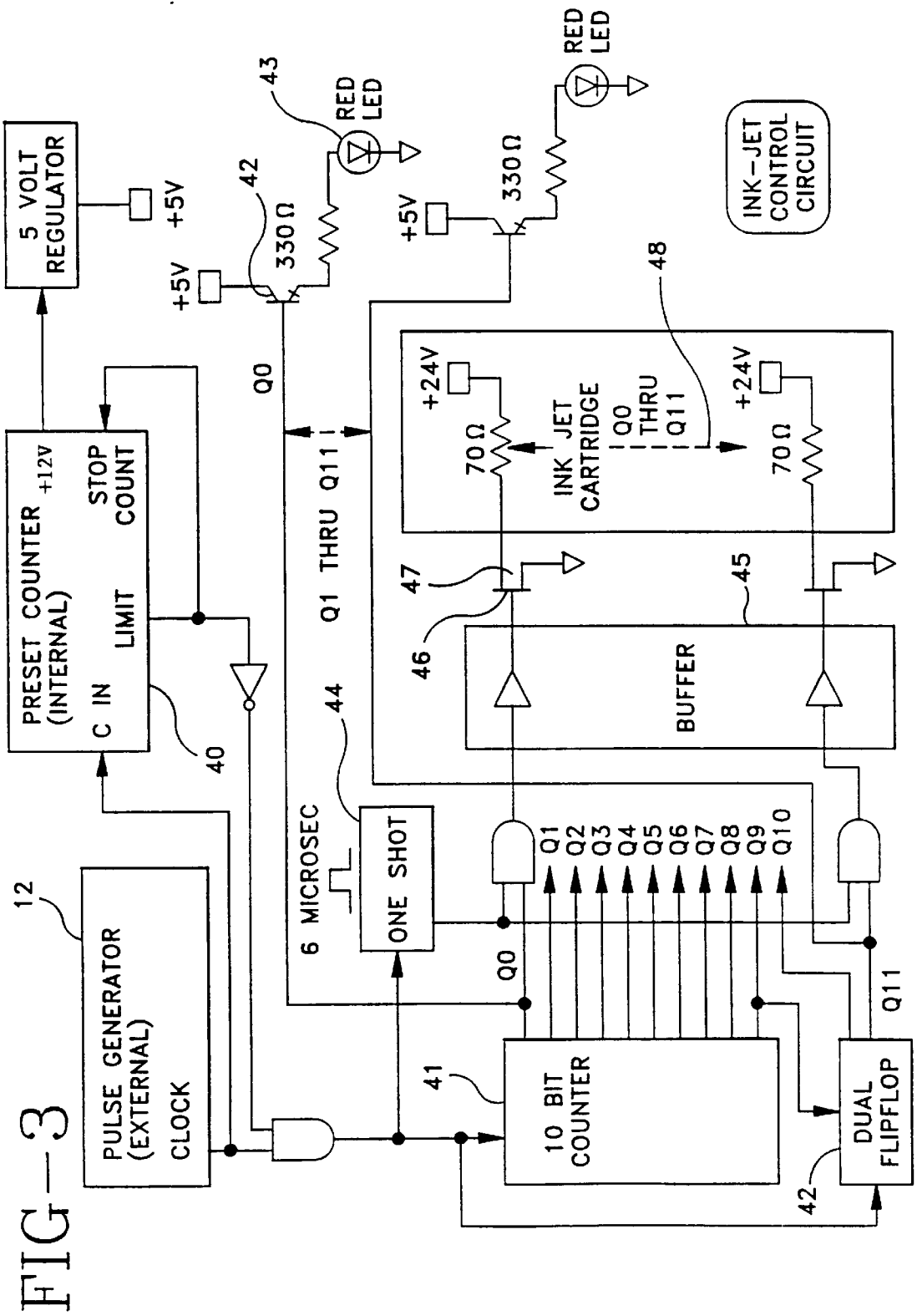
FIG. 3 is a circuit diagram of a circuit included in a preferred embodiment of the present invention.

Referring now to the flow chart of FIG. 3 in conjunction with FIGS. 1 and 2, two conceptually separate units are employed together to cause the droplet generator 10, e.g. ink-jet cartridge, to emit droplets at the rate and number the user desires. A pulse generator 12 is used to set the frequency at which a pulse controller 14 distributes and sends voltage pulses suitable for firing the nozzles 17. The pulse generator can be an outboard-type pulse generator or a built-in pulse generator. One pulse generator (PG) suitable for this purpose is an Avtech model AV-1002-C, due to its low cost and built in manual push-button arrangement. The PG output is adjustable in terms of frequency and pulse width. A pulse width of about 500 microseconds was found to be suitable over the range of 1 to 1000 pulses per second. The transistor to transistor logic or TTL (0–5 volt) output of the PG was used to ensure that correct logic levels were maintained at all times, and that no baseline offset inadvertently occurred.

Once the output of the PG enters the pulse controller, it initially passes to a counter 40 such as a Veeder-Root Model 7910 Predetermining Counter having a presettable counter function which the user sets from the front panel. The counter totals the number of pulses it has received. When the preset limit is reached, the control output goes to a high state, where it remains until the user resets the counter. When the control output goes high, no further pulses are able to pass to the system, therefore no droplets can be generated. This is accomplished by first inverting the logic of the control output, and then doing a logical AND (using a 2-input CD4081 AND gate) with the output of the PG.

If the preset limit has not been reached, the output of the PG passes through the AND gate unhindered, where it then acts as the clock input for the rest of the system. It initially passes to a second counter 41 such as a Decade Counter (CD4017) which operates in tandem with two flip-flops 42 (CD4013) to extend its counting capability to 12 bits. The counter chosen for this design can be a Johnson type counter, in which one of 12 outputs goes high for a full clock period, in sequential order, every time a clock pulse is received. In this design, each output from the counter corresponds to one of the nozzles on the ink-jet cartridge, and is a controlling mechanism for it. Therefore, the high output from the counter will determine which nozzle will produce a droplet.

When a counter output goes high, it triggers a [2N2222] transistor 42, which powers an LED 43 on the front display panel to light up for one clock cycle, demonstrating for the user the active nozzle. The outputs of the counter are then logically ANDed with the output of a pulse generator 44 such a One-Shot (CD4047), which produces a 6 microsecond pulse once every clock pulse. Because the CD4047 is triggered on the falling edge of the clock pulse, it does not produce a pulse until well after the output of the Johnson Counter (CD4017) has gone high, thereby alleviating a potential timing problem. This operation then results in a 6 microsecond pulse on only the output of the counter which is high (all other outputs will be low, or inactive). This output then passes through a buffer 45 (CD4503) to increase its current driving capability, and then to the gate 46 of a 2N6782 Transistor 47 where it turns on the transistor for 6 microseconds, allowing 24 volts to be applied to the selected 70 ohm resistor pad 48 in the ink jet cartridge. This causes a small volume of test sample to vaporize, and the resulting increase in pressure causes a liquid droplet 19 to be forced out of the nozzle 17.

Figure 4:
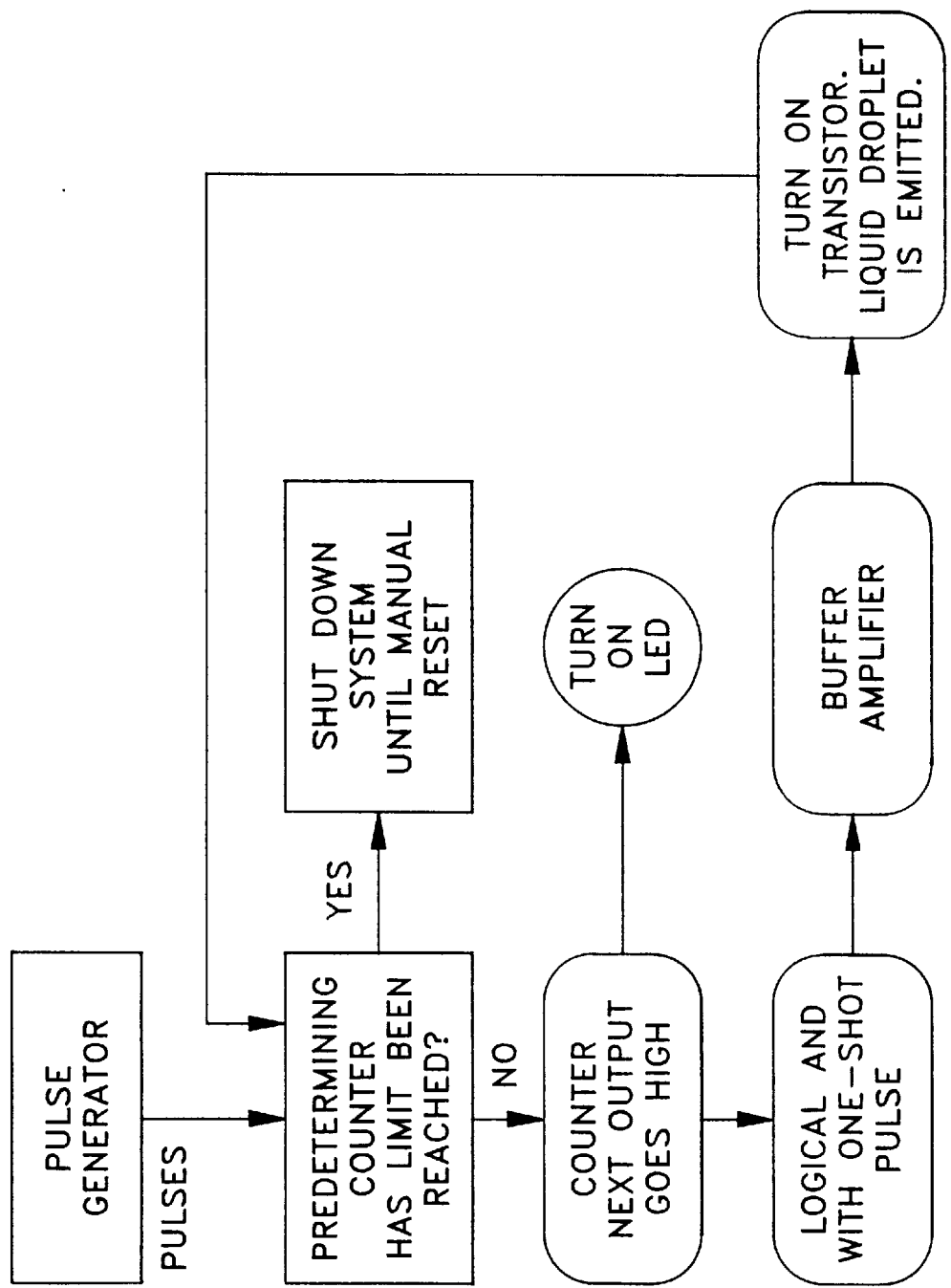
FIG. 4 is a flow diagram illustrating electronic generation of a sample-containing droplet using an apparatus of the present invention.

The next clock pulse from the PG begins the cycle over again, where it again passes through the predetermining counter. If the limit has not been reached, the pulse passes to the Johnson counter where the next output in sequence goes high. This output then turns on the LED and transistor, and emits a droplet from the next nozzle. This sequence of events repeats until the counter has determined that the preset number of pulses (or droplets) has been reached, at which point the control output goes into a high state, and prevents any further pulses from reaching the Johnson counter. The foregoing is also described in a flow chart. See FIG. 4.

In another aspect of the invention there is provided a method of generating low concentration aerosols having a known particle size. This method includes:

a) generating liquid droplets which contain sample particles;

b) drying the liquid droplets so that only the dried sample particles remain; and c) directing the sample particles to an analyzing instrument, preferably at a low velocity.

As pointed out above, the sample of interest can be agglomerates of bacteria cells or spores which are often part of a biological warfare agent. The exiting particle is directed to a sample analyzer by facilitating communication of the exit orifice of the delivery tube with the sample entry port of the analyzer. It is to understood that the connection of the tube to the analyzer must be such that it does not destroy the velocity of the particle or otherwise alter the physical properties of the sample particle.

What is claimed is:

1. A low concentration aerosol generating apparatus for generating a predetermined count of biological agent particles for calibrating a biological detection instrument which comprises:

a substantially hollow drying chamber having a first end, a second end, and a gas circulation means for circulating a gas in a flow through said drying chamber via an inlet means and an outlet means;

an aerosol droplet generator connected to said first end of said drying chamber, said generator containing a liquid medium having a biological agent dispersed therein, and including nozzle outlet means and being capable of generating principal aerosol droplets of said liquid medium having a biological agent constituent from said nozzle outlet means of a predetermined size within said drying chamber;

means controlling said aerosol droplet generator for generating a predetermined count of said principal aerosol droplets;

a delivery tube within said drying chamber, said delivery tube having a first orifice arranged within said drying chamber in substantial vertical alignment with said nozzle outlet means for receiving said principal aerosol droplets and a second orifice for allowing said principal aerosol droplets upon being dried to exit said drying chamber as a sequence of substantially dried biological agent particles, with the distance between said nozzle outlet means and said first orifice being no greater than the stop distance for the principal aerosol droplets being generated but greater than the stop distance for any smaller secondary liquid fragments released by the nozzle outlet means to enable said primary aerosol droplets to enter the delivery tube while preventing any smaller secondary liquid fragments emitted from the nozzle outlet means from entering the delivery tube whereby the predetermined count of substantially dried biological agent particles is achieved for calibration purposes; and said gas circulation means having means for generating and regulating said flow of said gas through said drying chamber.

2. The apparatus of claim 1, further comprising means for heating said delivery tube.

3. The apparatus of claim 1, wherein said inlet means comprises an orifice in said second end of said drying chamber.

4. The apparatus of claim 1, wherein said outlet means comprises an orifice in said first end of said drying chamber.

5. The apparatus of claim 1, wherein said aerosol nozzle means includes a plurality of nozzles capable of generating said sample containing droplets.

6. The apparatus of claim 5, wherein said nozzles are controlled by a pulse generator.

7. The apparatus of claim 1, wherein said means for generating said gas flow is a pump.

8. The apparatus of claim 1, wherein said means for regulating said flow is a flowmeter for adjusting said flow.

9. The apparatus of claim 1, wherein said gas is air.

10. The apparatus of claim 1, wherein said gas circulation means comprises a substantially continuous flow of said gas from said inlet means to said outlet means of said drying chamber.

11. The apparatus of claim 10, wherein said gas circulation means further comprises a desiccant positioned prior to said inlet means.

12. The apparatus of claim 10, wherein said gas circulation means further comprises an air filter positioned prior to said inlet means.

13. The apparatus of claim 1, further comprising means for counting said samples generated by said aerosol droplet generator.

14. The apparatus of claim 1, wherein said aerosol droplets have a diameter of from about 2 to about 10 microns.

15. The apparatus of claim 1 further including electrical heating tape wrapped around said delivery tube.

16. The apparatus of claim 1, wherein said sample comprises agglomerates of bacteria cells.

17. The apparatus of claim 1, wherein said sample comprises spores.

* * * * *